United States Patent [19]

Schumann

[11] Patent Number: Plant 5,370

[45] Date of Patent: Dec. 18, 1984

[54] GERANIUM PLANT NAMED FORTUNA

[75] Inventor: Ingeborg Schumann, Bad Ems, Fed. Rep. of Germany

[73] Assignee: Pelargonien-Fischer KG, Hillscheid, Fed. Rep. of Germany

[21] Appl. No.: 547,895

[22] Filed: Nov. 2, 1983

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Koch

[57] ABSTRACT

A new and distinct cultivar of geranium plant named Fortuna characterized by the combined features of red flower color and single flower form, excellent branching, good chlorophyll quality, and low temperature tolerance.

2 Drawing Figures

The present invention comprises a new and distinct cultivar of geranium, botanically known as *Pelargonium zonale,* and hereinafter referred to by the cultivar name Fortuna.

Fortuna is a product of planned breeding program which had the objective of creating new geranium cultivars having vermilion red flower color, good branching, better chlorophyll quality for better transportation, and better temperature tolerance.

Fortuna was originated from a hybridization made in a controlled breeding program in Hillscheid, Federal Republic of Germany in 1977. The female parent was an unpatented cultivar named Hillscheider Trumpf, characterized by its early flowering, fast rooting, semi-double flowers, and strong zonation. The male parent of Fortuna was the unpatented cultivar Vesuv, a cultivar having a compact habit and short internodes.

Fortuna was discovered and selected as one flowering plant within the progeny of the stated cross by Ingeborg Schumann on July 14, 1978 in a controlled environment in Hillscheid, Federal Republic of Germany.

The first act of asexual reproduction of Fortuna was accomplished when vegetative cuttings were taken from the initial selection in January 1979 in a controlled environment in Hillscheid, Federal Republic of Germany by a technician working under formulations established and supervised by Ingeborg Schumann. Horticultural examination of selected units initiated in the Spring of 1979 and continuing to 1982 has demonstrated th the combination of characteristics as herein dis- ed for Fortuna are firmly fixed and are retained through successive generations of asexual reproduction.

Fortuna has not been observed under all possible environmental conditions. The phenotype may vary significantly with variations in environment such as temperature, light intensity, and day length. The following observations, measurements, and comparisons describe plants grown in Hillscheid, Federal Republic of Germany under greenhouse conditions which approximate those generally used in commercial practice.

The following traits have been repeatedly observed and are determined to be basic characteristics of Fortuna which in combination distinguish this geranium as a new and distinct cultivar:

1. Dutch vermilion red flower.
2. Single flower form.
3. Leaf zonation.

4. Good chlorophyll quality for transportation.
5. Temperature tolerance for cultivation below 12° C.
6. Excellent branching, producing an average of 4.2 branches per plant.

Of the many commercial cultivars known to the present inventor, the most similar in comparison to Fortuna is the unpatented cultivar Bundeskanzler. Reference is made to attached Chart A which compares certain characteristics of Fortuna to those same characteristics of Bundeskanzler. In general comparison to Bundeskanzler, Fortuna has improved shatter resistance, good chlorophyll quality, low temperature tolerance, a more round flower form, and better branching.

The accompanying photographic drawings show typical flower and foliage characteristics of Fortuna, with colors being as true as possible will illustrations of this type. Sheet 1 is a color photograph of the flower buds and foliage of Fortuna, and sheet 2 is a black and white print showing the underside of the foliage.

In the following description color references are made to The Royal Horticultural Society Color Chart, and in certain instances to the Horticultural Color Chart (H.C.C.). The color values were determined between 2:50 and 3:05 P.M. on Aug. 11, 1983 under 25,000 Klux at Hillscheid, Federal Republic of Germany.

CLASSIFICATION

Botanical: A hybrid of the genus *Pelargonium l'hert.*
Commercial: Fortuna.

INFLORESCENCE

Umbel:

*Average diameter.*—113 mm.
*Average depth.*—83 mm.
*Peduncle length.*—172 mm.
*Pedical length.*—29 mm. (⅔ strength anthocyan to treat pedicel swelling).

Corolla:

*Average diameter.*—52 mm.
*Form.*—Single.
*Color (general tonality from a distance of three meters).*—R.H.S. 44B, H.C.C. 717.
*Color (abaxial).*—R.H.S. 44B, H.C.C. 717 (sepals with anthocyan).
*Color (adaxial).*—H.C.C. 17.

Bud:

*Shape.*—Narrow elliptic.

*Color(abaxial).*—Light red.

Reproductive organs:

*Androecium.*—Monodelphous; 7 stamens; plentiful pollen.

*Gynoecium.*—5-lobed stigma.

Spring flowering response period: In Hillscheid, Federal Republic of Germany in 1982, 45% of plants with at least 1 flower opened 13 weeks after planting or unrooted cuttings.

Outdoor flower production: The flower count in 1982 in Hillscheid, Federal Republic of Germany indicated between 48 and 52 flowers per plant for June through October observation period.

Durability: Very good.

PLANT

Foliage:

*Form.*—Kidney shaped, carried on medium short leaf stem.

*Margin.*—Bicrenate.

*Color (abaxial).*—Medium green.

*Color (zonation).*—Brown.

*Tolerance to botrytis.*—Good.

General appearance and form:

*Internode length.*—27 mm.

*Branching pattern.*—Excellent, producing an average of 4.2 branches per plant.

*Height.*—240 mm.

CHART A

| | Bundeskanzler | Fortuna |
|---|---|---|
| Chlorophyll Quality | bad | good |
| Durability Shatter Resistance | bad | good to medium |
| Flower Form | more zygomorphic | more rotate (actinomorphic) |
| Pedicel Swelling | no | present |
| Low Temperature Tolerance | bad | good |
| Salt Tolerance | bad | good |
| Branching Habit (Number of branches) | 3.2 | 4.2 |

I claim:

1. A new and distinct cultivar of geranium plant named Fortuna, as described and illustrated, and particularly characterized by the combined features of red flower color and single flower form, excellent branching, good chlorophyll quality, and low temperature tolerance.

* * * * *

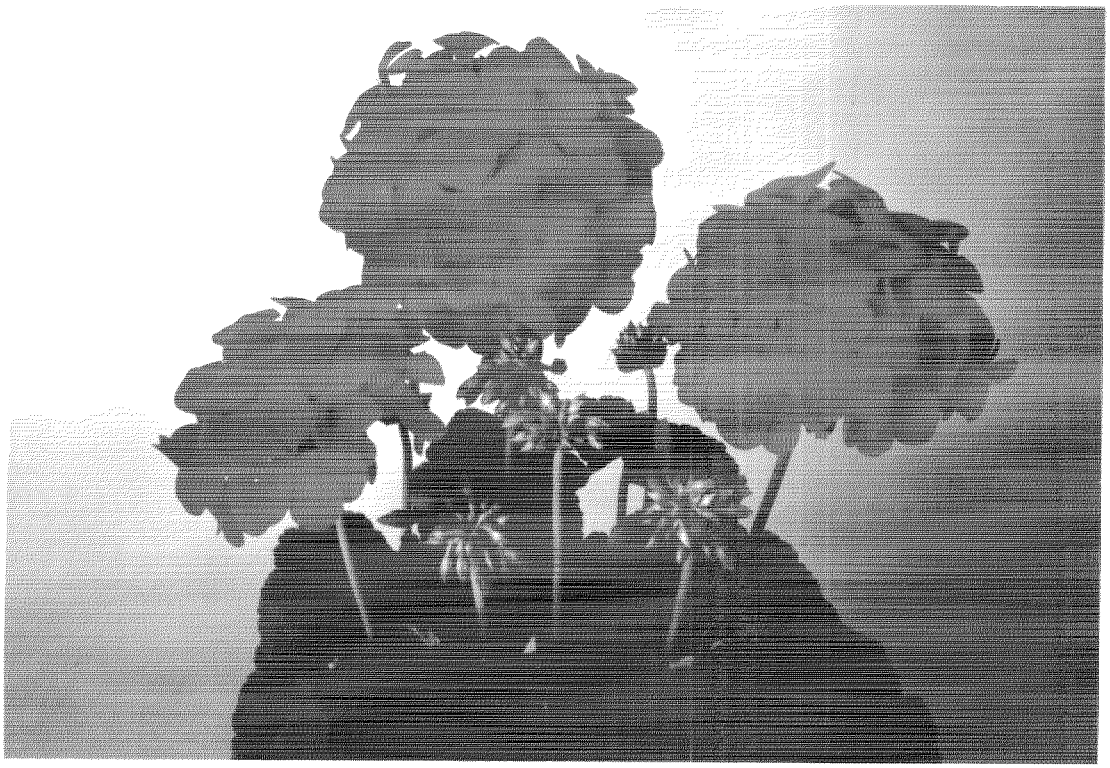

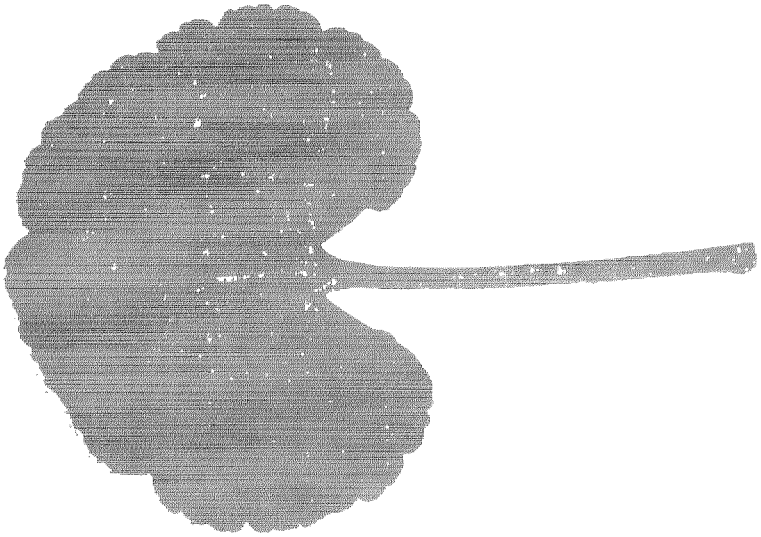
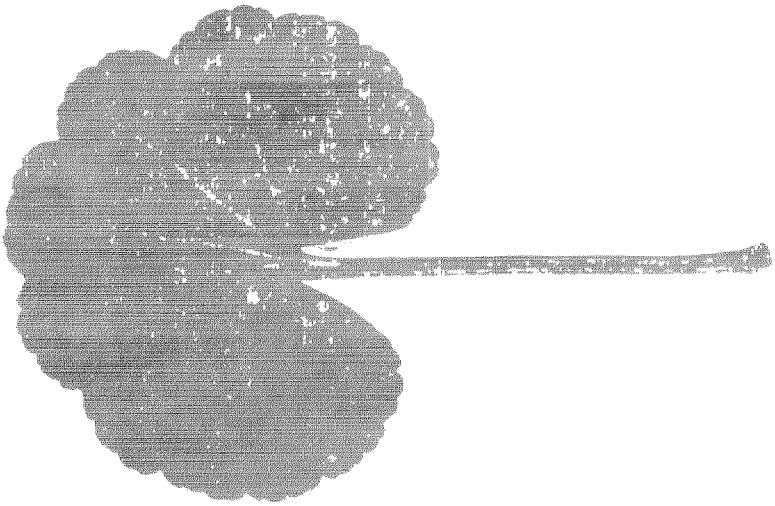

Fortuna